United States Patent
Warr et al.

(10) Patent No.: US 6,962,983 B2
(45) Date of Patent: Nov. 8, 2005

(54) PROCESS FOR THE PREPARATION OF DIAZOMETHANE

(75) Inventors: Antony John Warr, Chester (GB); Lee Proctor, Maeshasn (GB)

(73) Assignee: Phoenix Chemicals Limited, Bromborough (GB)

( * ) Notice: Subject to any disclaimer, the term of this patent is extended or adjusted under 35 U.S.C. 154(b) by 190 days.

(21) Appl. No.: 10/129,404

(22) PCT Filed: Dec. 15, 2000

(86) PCT No.: PCT/GB00/03563

§ 371 (c)(1),
(2), (4) Date: May 2, 2002

(87) PCT Pub. No.: WO01/47869

PCT Pub. Date: Jul. 5, 2001

(65) Prior Publication Data

US 2002/0188112 A1 Dec. 12, 2002

(30) Foreign Application Priority Data

Dec. 23, 1999 (GB) .......................... 99304545

(51) Int. Cl.⁷ .......................... C07C 245/16
(52) U.S. Cl. ..................... 534/565; 534/558
(58) Field of Search ................. 534/558, 565

(56) References Cited

U.S. PATENT DOCUMENTS

| | | | |
|---|---|---|---|
| 2,675,378 A | * 4/1954 | Fawcett | 534/565 |
| 5,459,243 A | 10/1995 | Acevedo et al. | 534/565 |
| 5,817,778 A | 10/1998 | Archibald et al. | 534/565 |
| 5,854,405 A | 12/1998 | Archibald et al. | 534/565 |

FOREIGN PATENT DOCUMENTS

| | | |
|---|---|---|
| EP | 0 916 648 A1 | 5/1999 |
| EP | 0 916 649 A1 | 5/1999 |

OTHER PUBLICATIONS

Proctor et al., "Development of a Continuous Process for the Industrial Generation of Diazomethane", Organic Process Research and Development, 6, 884–892, 2002.*

Bernd–Eistert, "Synthesis with Diazomethane", 513–570, no date provided.

Black, T.H., "The Preparation and Reaction of Diazomethane," Aldrichimica Acta 16(1) 3–10 (1983).

Chemistry in Industry, Feb. 21, 1994, p. 122/123, Nov. 5, 1990.

De Boer, T.H. J., and Backer, H. J., "A New Method for the Preparation of Diazomethane," Recueil 73, 229–234 (1954).

Yamaguchi, Masato (Kurita Water Industries, Ltd.), "Preparation of diazomethane ether solution," Chemical Abstracts, vol. 110, No. 5, Jan. 30, 1989, Columbus, OH, U.S., Abstract No. 38611c.

Ruehle et al., Chemical Abstracts, vol. 91, No. 19, Nov. 5, 1979 Columbus, OH, US, Abstract No. 157184.

* cited by examiner

Primary Examiner—Fiona T. Powers
(74) Attorney, Agent, or Firm—David A. Farah; Sheldon & Mak PC

(57) ABSTRACT

A method for the production of diazomethane comprising the steps of a) feeding a base and a diazomethane precursor into a reactor vessel; b) generating gaseous diazomethane by allowing the base and the gaseous diazomethane precursor to react; and c) removing the gaseous diazomethane using a diluent gas.

45 Claims, 1 Drawing Sheet

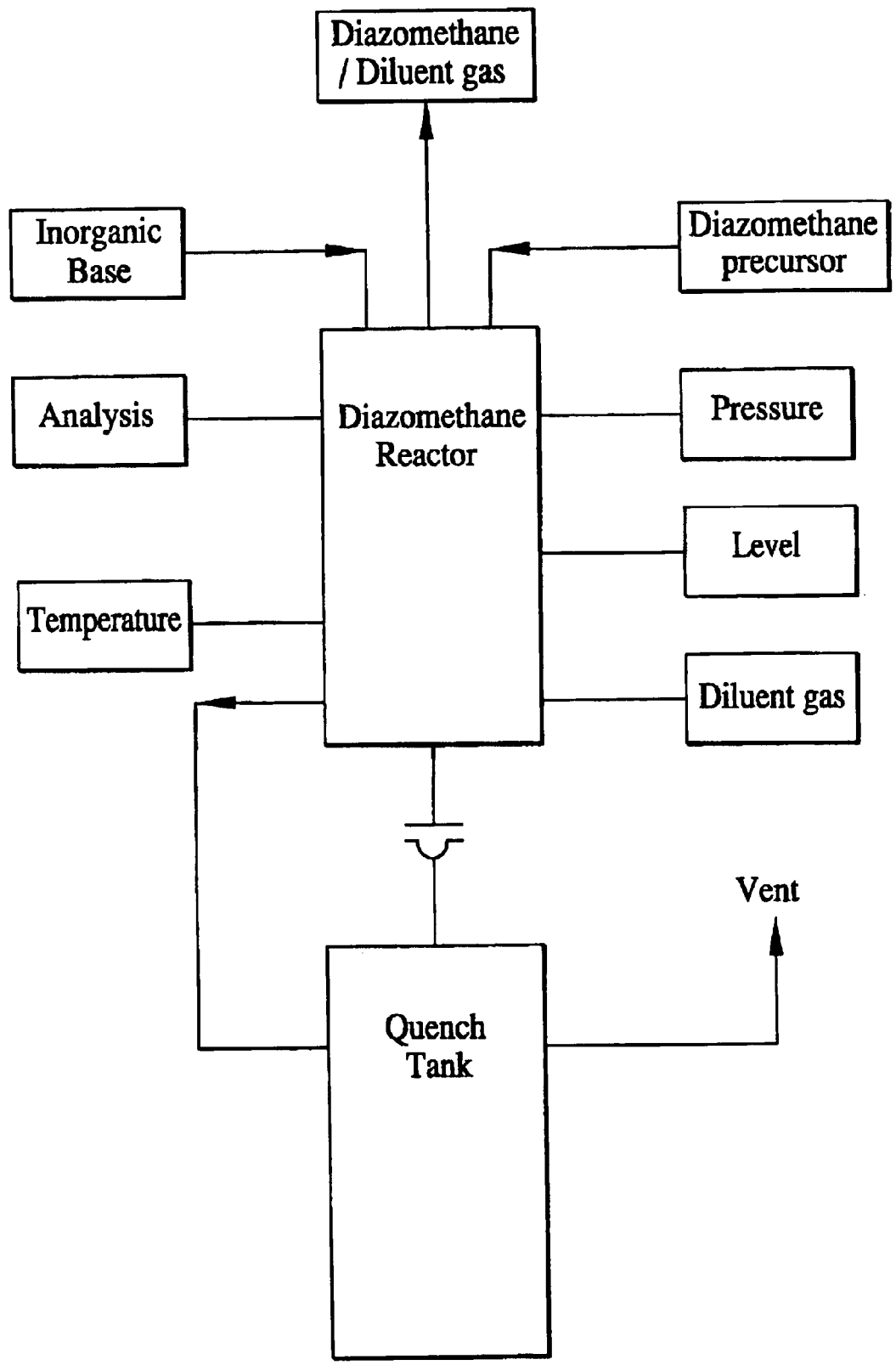

PROCESS FOR THE PREPARATION OF DIAZOMETHANE

CROSS-REFERENCE TO RELATED APPLICATIONS

This application claims the benefit of PCT Application No. PCT/GB00/03563 filed Dec. 15, 2000, and claims the benefit of United Kingdom Application No. GB 9930454.5 filed Dec. 23, 1999, the contents of which are incorporated by reference in this disclosure in their entirety.

BACKGROUND

Diazomethane ($CH_2=N=N$, also known as azimethylene or diazirine) is a highly reactive gas with a wide range of utility in chemical syntheses. It reacts rapidly with carboxylic acids to form the corresponding methyl esters, generally in high yield, with the evolution of gaseous nitrogen. In like manner diazomethane reacts with phenols, enols and alcohols to form methyl ethers with concomitant release of nitrogen; the rate of reaction depending on the acidity of the substrate. A further example of its use is the formation of carbon to carbon bonds with substrates such as acid chlorides and anhydrides. The so formed diazoketones are themselves useful intermediates. Further examples are its use in cycloaddition reactions with olefins to form cylopropanes and nitrogen heterocycles. Similarly chain extension or ring expansion of ketones and conversion of ketones to epoxides can be readily achieved with diazomethane. Still further examples of its use include formation of viral protease inhibitors. A number of viral protease inhibitors including those used to combat HIV are derived from three-carbon amino acid isosteres. An example of these viral protease inhibitors is Nelfinivir Mesylate (Agouron Laboratories). The crucial three-carbon fragment can be built from a two-carbon functionalized amino acid using diazomethane in a modified Arndt-Eistert reaction. This approach is particularly attractive since reaction with diazomethane does not compromise the chiral integrity of the amino acid.

Diazomethane is a powerful carcinogen, allergen and is highly poisonous. However the principle impediment to its use is that it is highly explosive. While the toxic properties of diazomethane can be obviated by judicious plant design and good manufacturing practice, its sensitivity to explosion places greater restraints on its use. The technical literature for the lab-scale synthesis of diazomethane cautions against the use of ground-glass joints and specifically designed firepolished glassware is recommended. The Aldrich Chemical Company, Inc., Milwaukee, Wis., USA markets a "large-scale" DIAZALD® apparatus capable of generating a solution of up to 300 millimoles of diazomethane in diethyl ether by single batch reaction. See Black, T. H., "The Preparation and Reactions of Diazomethane," Aldrichimica Acta 16(1) 3–10 (1983).

A "large-scale" preparation is disclosed by Acevedo et al in U.S. Pat. No. 5,459,243, "Apparatus and Processes for the Large Scale Generation and Transfer of Diazomethane," issued Oct. 17, 1995. The reactions disclosed are performed on the 100 millimole scale and generate dilute solutions of diazomethane in dichloromethane.

A batch process for the production of gaseous diazomethane, "A New Method for the Preparation of Diazomethane" is disclosed by De Boer, T. H. J., and Backer, H. J. See Recueil 73 229–234 (1954). The process comprises introducing a solution of potassium hydroxide in a mixture of Carbitol—water to p-toly sulphonylmethylnitrosamide in anisole. A gentle flow of nitrogen is passed through the apparatus and the liberated gaseous diazomethane is obtained in 48% yield. The paper goes on to disclose that when the diazomethane was absorbed immediately in an excess of benzoic acid in ether, the yield was 63%.

More recently Chemistry in Industry, 21 Feb. 1994, page 122/123, in a follow up letter to a publication in the same journal dated 5 Nov., 1990, cautions against the production of gaseous diazomethane because of the explosive risks. This is consistent with Bernd Eistert—"Synthesis with Diazomethane" which states "Gaseous diazomethane, even on dilution with nitrogen, likewise can undergo explosive decomposition, especially at temperatures of 100° C. or higher".

Indeed it is because of the explosive nature of gaseous diazomethane that the skilled man has tended towards production and use of diazomethane in dilute solutions.

Aerojet—General Corporation ("Aerojet") is the only company to date to have published procedures to produce diazomethane on a truly large scale.

A large-scale batch production process for the production of solutions of diazomethane is disclosed by Aerojet in U.S. Pat. No. 5,817,778, "Large Scale Batch Process for Diazomethane," issued Oct. 6, 1998 and European Patent Publication No. EP 0 916 649 A1, "Large Scale Batch Process for Diazomethane," published can 19 1999. Preparations of diethyl ether solutions of diazomethane are disclosed on the 50 gram-mole to 25,000 gram-mole scale.

A continuous process for the production of solutions of diazomethane has been disclosed by Aerojet in U.S. Pat. No. 5,854,405, "Continuous Process for Diazomethane from an N-methyl-N-Nitrosamine and from Methylurea through N-Methyl-N-Nitroso Urea," issued Dec. 24, 1998 and European Patent Publication No. EP 0 916 648 A1, "Continuous Process for Diazomethane," published can 19 1999. This procedure involves dissolving an N-methyl N-nitroso amine in a mixture of two organic solvents—one of which is at least partially water miscible and dissolves the N-methyl-N-nitrosoamine, and the other is one that is substantially less water-miscible than the first and forms a separate phase with water and dissolves diazomethane. A stream of this solution is combined with a stream of an aqueous inorganic base, the aqueous and organic phases are permitted to settle after a suitable residence time and the phases are separated, the diazomethane being recovered as an organic solution. It is stated that because all the stages of the process can be conducted in the liquid phase, the formation of diazomethane vapor is avoided and the risk of detonation is reduced or eliminated. However, the process isolates the diazomethane in a flammable organic solvent which provides a fire risk.

In view of the versatility of diazomethane and its associated hazards a safe and efficient large-scale continuous process providing good yields and preferably obviating the need for volatile and flammable solvents while maintaining a low overall inventory of diazomethane is desirable.

FIGURES

These and other features, aspects and advantages of the present invention will become better understood with regard to the following description, appended claims, and accompanying FIGURE where:

FIG. 1 is a schematic diagram of a process according to the present invention.

DESCRIPTION

While the invention will be described in connection with certain preferred embodiments, it is not intended to limit the invention to the particular embodiments. On the contrary, it is intended to cover all alternatives, modifications and equivalent processes as can be included within the spirit of the invention as defined by the appended claims.

The applicant has experimentally determined that the lower explosive limit (LEL) of diazomethane is 3.9%. (The LEL is a limit defined in air). By "diluting" the diazomethane in an inert gas such as nitrogen the explosive limit is increased to an experimentally determined value of, in the case of nitrogen, 14.7% allowing the applicant to operate at higher concentrations of diazomethane safely.

According to the present invention there is provided a continuous method for the production of diazomethane comprising the steps of feeding:

a diazomethane precursor, and a base into a reactor vessel where they react to generate diazomethane, and removing the resulting diazomethane as a gas.

In order to maintain a steady state operation the resultant waste steam is removed. The waste stream can comprise any unreacted reactants, by-products of the reaction, solvents and any residual diazomethane remaining in solution.

Preferably the diazomethane precursor and the base are co-fed into the reactor vessel in a continuous stream and the diazomethane gas and the resultant waste stream are removed from the reactor vessel in a continuous manner. Alternatively the diazomethane precursor and base can be fed into the reactor vessel as intermittent or pulsed streams and the diazomethane gas and the waste stream can be removed from the reactor vessel as intermittent or pulsed streams.

Preferably the diazomethane precursor is dissolved in a first solvent and the base is dissolved in a second solvent.

It is however possible for the base to be fed into the reactor vessel in a solid form and/or a liquid diazomethane precursor to be selected thereby obviating the need for one or more of the first and second solvents.

In yet another embodiment the first solvent and second solvent are one of the same solvent or a mixture of the first and second solvent.

Preferably the generation and removal of diazomethane gas is aided/effected by the use of a sparge diluent gas, which can be introduced above (top-surface) and/or below (sub-surface) the reaction mixture. A sub-surface sparge diluent gas aids the mixing of the reaction mixture and helps displace the diazomethane gas from the reaction mixture. A top-surface diluent sparge further assists to displace the diazomethane gas. Both the top-surface and bottom surface sparges act as diluents and are adjusted to achieve the desired operating conditions.

Preferably the flow rates of the sparge diluent gas are such that the concentration of diazomethane gas is maintained below the explosive for the diazomethane in said sparge diluent gas.

When the sparge diluent gas is nitrogen the concentration of diazomethane in nitrogen is preferably maintained at below 14.7%.

Preferably the diazomethane generated—and displaced by the diluent sparge gas—is continuously reacted with the intended substrate at a rate which minimizes the inventory of diazomethane within the reaction system.

By controlling the temperature of the reaction and controlling the flow rates of one or more of:

the diazomethane precursor;

the base;

the sparge diluent gas; and the waste stream a steady-state operation can be achieved at a given set of reaction conditions. By maintaining the relative concentration of the reactants at a steady state, high yields and high purity diazomethane can be obtained.

The optimum steady state conditions are primarily a function of the rate of addition of the reactants (and any respective solvents used to introduce them into the reactor vessel), their respective concentrations in the reactor vessel, the rate at which the diluent sparge gas is fed into the reactor vessel, the reaction temperature and the rate at which the waste stream and diazomethane gas are removed.

By monitoring the concentration of the resulting diazomethane gas, the process can thus be controlled to achieve the desired operating conditions, for example, by controlling one or more of the factors effecting steady state, to optimize production and maintain safe operability.

In most cases the ratio of the base to diazomethane precursor is maintained at from, for example, 1.0 to 1.5:1 molar equivalents.

More preferably the ratio of base to diazomethane precursor is maintained in excess at from about 1.1 to 1.4:1 molar equivalent, and most preferably at about 1.2:1 molar equivalents.

Preferably the diazomethane precursor is an N-methyl N nitroso compound or a precursor thereof.

The preferred N-methyl N nitroso compounds are selected from the group consisting of N-methyl-N-nitroso-p-toluenesulphonamide; N-methyl-N-nitroso urea; N-nitrosomethylaminoisobutyl methyl ketone; N,N'-dimethyl-N,N'dinitrosoterephthalamide; -[N'-methyl-N'nitroso (aminomethyl)]benzamide and 1-methyl-3-nitro-1-nitrosoguanadine.

The preferred diazomethane precursor is N-methyl-N-nitroso-p-toluenesulphonamide.

The first solvent is preferably selected to:

i) be non volatile, i.e. have a low vapor pressure;

ii) have a high boiling point;

iii) be non-flammable; and iv) be water soluble.

By non-volatile it is preferred that the vapor pressure is below 5 mm at 25° C. and most preferably below 1 mm at 20° C.

By high boiling point it is preferred that the boiling point is above 95° C., most preferably above 150° C.

By non-flammable it is preferred that the flash point is above 55° C. as defined under the UK Chemicals (Hazard Information for Packaging & Supply) Regulations 1994.

The preferred first solvents are shown in the table below which additionally give their flashpoint, boiling point and vapor pressure.

TABLE

| SOLVENT | FLASH POINT (° C.) | BOILING POINT (° C.) | VAPOR PRESSURE |
|---|---|---|---|
| Di(ethylene glycol) ethyl ether | 96 | 202 | 0.08 mm (20° C.) |
| N,N'Dimethylformamide | 58 | 153 | 3.9 mm (25° C.) |
| N,N'Dimethylacetamide | 70 | 153 | 2 mm (25° C.) |
| Hexamethylphosphoramide | 105 | 231 (740 mm) | 0.07 mm (25° C.) |

TABLE-continued

| SOLVENT | FLASH POINT (° C.) | BOILING POINT (° C.) | VAPOR PRESSURE |
|---|---|---|---|
| Dimethyl suphoxide | 96 | 189 | 0.42 mm (20° C.) |
| Tetramethylene sulphone | 165 | 285 | 0.01 mm (20° C.) |

They can be used alone or as mixtures of one or more of these with or without a second solvent.

The most preferred first solvent is dimethyl suphoxide.

The base can be an inorganic or organic base.

The preferred bases are inorganic bases, such as, for example, sodium, potassium and barium hydroxide. Most preferred is potassium hydroxide.

Organic bases which are suitable include, for example, sodium and potassium methoxide, sodium and potassium ethoxide, sodium isopropoxide, sodium cyclohexoxide and quaternary ammonium or quaternary phosphonium hydroxides or alkoxides such as tetra-n-butylammonium hydroxide, cetylpyridinium hydroxide, benzyltrimethylammonium ethoxide, tetraethylphosphonium hydroxide, and n-butyltriethylphosphonium phenoxide.

The second solvent is preferably a polar solvent, most preferably water or a mixture of polar solvents either with or without a first solvent.

In some cases the first and second solvent are one of the same solvent or a mixture of the first and second solvents.

The sparge diluent gas can be any suitable gas that displaces or effects removal of the resulting diazomethane from the reaction mixture. Examples include nitrogen, helium, argon, carbon dioxide and air. Inert gases are preferred, and the most preferred is nitrogen.

Preferably a reaction temperature is maintained at between 25° C. and 70° C., most preferably at about 40° C.

Any residual diazomethane which remains in the reaction mixture and is not removed as a gas, is destroyed by passing the waste stream, into a quench tank containing an acid medium. Preferably the waste stream is a single phase aqueous waste stream.

The pH of the acid medium is preferably between pH 4 and 6, most preferably about pH 5.5. The preferred acid is acetic acid although any suitable inorganic or organic acid could be used.

The steady state is controlled by reference to the yield and purity of the resulting diazomethane gas and its concentration in the diluent gas.

The invention, and more particularly the selection of preferred features overcome a number of problems or disadvantages associated with the known large scale processes for producing diazomethane. Some of the problems and/or disadvantages associated with such processes are set out below:

They generally employ flammable or highly flammable solvents;

They employ highly volatile solvents;

They require a relatively large inventory of diazomethane;

The processes generally require condensation of the diazomethane/solvent vapor stream;

The processes are bi-phasic and require efficient mixing and subsequent separation by distillation or phase separation; and The processes generate solutions of diazomethane, which can limit the flexibility of the downstream chemistry.

The batch process requires mechanical agitation with the incumbent risk of hot spots, leaking stirrer glands and also requires the use of a phase transfer catalyst to achieve improved yields.

The benefits of the method of the invention and more particularly the preferred features of the invention are set out below:

The diazomethane is generated quickly and continuously removed and reacted in downstream chemistry. The process therefore operates with a very low inventory of diazomethane, minimizing the principal explosive hazard; and the diazomethane so generated is substantially free of solvents, moisture and other contaminants. No additional drying of the diazomethane gas stream is necessary. The yield and purity of the diazomethane generated is very high and being substantially free of solvents and contaminants, allows flexible use in downstream chemical reactions.

The preferred solvents used in the process are non-volatile, have low vapor pressures, high boiling points, are non-flammable, and are water soluble. Environmental concerns arising from the process are therefore minimized.

The solvents used are chosen to ensure high solubility of the diazomethane precursor while minimizing the concentration of diazomethane in solution.

The reaction system is a homogenous/single-phase system. The generation of diazomethane is therefore extremely rapid without the need for any catalysts and the yield of diazomethane is in excess of 90%.

The diazomethane is generated in a reactor vessel of basic design. The reactor vessel is a dedicated unit which requires no mechanical agitation and has no moving parts.

Reactants can be continually co-fed into the reactor vessel. The addition rates can be accurately controlled allowing a steady state operation at the desired diazomethane concentration to be quickly achieved and maintained.

The diazomethane generated is continually "stripped" from the reactor using a top-surface and/or a subsurface diluent gas sparge. By controlling the rate of diluent sparge gas, the yield of diazomethane can be optimized By continually monitoring the generation, concentration and use of diazomethane on a real-time basis good steady-state process control can be achieved.

The process is highly flexible and very applicable to scale-up. Waste streams are continually rendered free of diazomethane by the application of aqueous acid. Treated waste is a homogenous single-phase and all components are soluble.

The invention will now be described in more detail by way of example only with reference to the FIGURE which is a schematic diagram of a process of the invention and the method outlined below.

Referring to the schematic diagram a feed tank was charged with a 15% (w/w) solution of potassium hydroxide. A second feed tank was charged with a 22.1% (w/w) solution of N-methyl-N-nitroso-p-toluenesulphonamide in dimethyl suphoxide. Both tanks were connected via pumps and/or pressure fed feed tanks to liquid mass flow meters. Full instrumentation control is provided for feeds, level/pressure, temperature and on-line analysis. The internal reactor surfaces are preferably polished to minimize rough surface issues. The reaction system has been specifically designed to promote laminar flow. The potassium hydroxide solution flow rate was set at 1.00 Kg/hour corresponding to a molar flow of potassium hydroxide of 2.67 mol/hour. The N-methyl-N-nitroso-p-toluenesulphonamide solution flow rate was set at 2.15 Kg/hour corresponding to a molar flow of N-methyl-N-nitroso-p-toluenesulphonamide of 2.22 mol/hour. Nitrogen was fed sub-surface and top surface through two mass flow controllers. The subsurface flow was set at a rate of 0.98 L/minute and the top-surface flow was set at a rate of 6.7 L/minute. Commencement of the diazomethane reaction caused the temperature of the reaction mixture to rise cooling was applied to maintain the reaction temperature at the desired set point of 40° C. The diazomethane/nitrogen stream was continually monitored to ensure the concentration of diazomethane in the gas phase remained constant and below the explosive limit. The flow-rates of top-surface and/or subsurface nitrogen, potassium hydroxide/water and N-methyl-N-nitroso-p-toluenesulphonamide/dimethyl suphoxide are adjusted to maintain the concentration of diazomethane at about 10%. Typically at least 96% of the diazomethane produced is removed in the gas phase.

The diazomethane generated was removed in the diluent gas sparge and continuously reacted in subsequent downstream chemistry to minimize the inventory of diazomethane in the reaction system. The reactor was continually drained in order to achieve a constant reactant mixture level and maintain a steady state operation. The waste stream which can contain residual levels of diazomethane was rapidly quenched into a tank containing 80% aqueous acetic acid. The pH of the tank was maintained at pH 5.5. Waste from the reactor, typically contains about 4% residual diazomethane. This procedure allows 90 g to 93 g of diazomethane to be produced per hour. The maximum inventory of diazomethane at any instance is 0.11 g.

The above reaction system is capable of producing 652 Kg of diazomethane per year at 80% utilization. By increasing the respective flow rates and adjusting the reactor volume, the system is capable of generating diazomethane at the rate of 5–10 kilos per hour (or 40 to 80 metric tonnes per year) while maintaining the inventory of diazomethane in the reaction system at under 100 g.

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. A method for the production of diazomethane comprising the steps of:
   a) feeding a diazomethane precursor dissolved in a first solvent and a base dissolved in a second solvent into a reactor vessel;
   b) generating gaseous diazomethane by allowing the base and the diazomethane precursor to react; and
   c) removing the gaseous diazomethane as a gas substantially free of solvent using a diluent gas.

2. The method of claim 1, further comprising the step of removing a waste stream from the reactor vessel.

3. The method of claim 1, where the waste stream is removed from the reactor vessel in a continuous stream.

4. The method of claim 1, where the feeding step comprises feeding either the diazomethane precursor, or the base, or both the diazomethane precursor and the base into the reactor vessel in a continuous stream; and.
   where the removing step comprises removing the gaseous diazomethane gas from the reactor vessel in a continuous stream.

5. The method of claim 1, where the waste stream is removed from the reactor vessel in an intermittent or pulsed stream.

6. The method of claim 1, where the diazomethane precursor is dissolved in a first solvent and the base is dissolved in a second solvent; and
   where the first solvent is the same as the second solvent.

7. The method of claim 1, where the diluent gas comprises a sparge diluent gas.

8. The method of claim 7, where the sparge diluent gas is introduced below the reaction mixture.

9. The method of claim 7, where the sparge diluent gas is introduce below the reaction mixture.

10. The method of claim 7, where the sparge diluent gas is introduced both above the reaction mixture and below the reaction mixture.

11. The method of claim 7, where the concentration of gaseous diazomethane gas is maintained in the sparge diluent gas at below the explosive limit for the gaseous diazomethane.

12. The method of claim 11, where the sparge diluent gas is nitrogen; and
    where the concentration of the generated gaseous diazomethane in the nitrogen is maintained at below about 14.7%.

13. The method of claim 1, where the amount of gaseous diazomethane generated is maintained at a steady state by controlling one or more than one rate selected from the group consisting of the rate of feeding the diazomethane precursor, the rate of feeding the base, and the rate of removal of the gaseous diazomethane.

14. The method of claim 1, where the reactor vessel is maintained at a temperature; and
    where the amount of gaseous diazomethane generated is maintained at a steady state by controlling the temperature.

15. The method of claim 1, where the amount of gaseous diazomethane generated is maintained at a steady state by controlling the rate of removal of the waste stream.

16. The method of claim 1, where the base and the diazomethane precursor are maintained in the reactor vessel at a ratio of from about 1.0 to about 1.5:1 molar equivalents of base:diazomethane precursor.

17. The method of claim 1, where the base and the diazomethane precursor are maintained in the reactor vessel at a ratio at about 1.2:1 molar equivalents of base:diazomethane precursor.

18. The method of claim 4, where the gaseous diazomethane generated is substantially insoluble in the first solvent.

19. The method of claim 5, where the gaseous diazomethane generated is substantially insoluble in the second solvent.

20. The method of claim 4, where the first solvent comprises a substance selected from the group consisting of dimethyl sulphoxide, di(ethylene glycol) ethyl ether, N,N'-dimethylformamide N,N'-dimethyl acetamide, hexamethylphosphoramide, tetramethylenesulphone and combinations of the preceding.

21. The method of claim 4, where the first solvent comprises a polar aprotic solvent.

22. The method of claim 4, where the first solvent comprises dimethyl sulphoxide.

23. The method of claim 1, where the base is an inorganic base.

24. The method of claim 1, where the base comprises a substance selected from the group consisting of sodium hydroxide and barium hydroxide.

25. The method of claim 1, where the base comprises potassium hydroxide.

26. The method of claim 1, where the base comprises an organic base.

27. The method of claim 1, where the base comprises a substance selected from the group consisting of potassium methoxide, sodium methoxide, potassium ethoxide, sodium ethoxide, sodium isopropoxide, sodium cyclohexoxide, a quaternary ammonium hydroxide, a quaternary ammonium alkoxide, a quaternary phosphonium hydroxide and a quaternary phosphonium alkoxides.

28. The method of claim 1, where the base comprises a substance selected from the group consisting of benzyltrimethylanmmonium ethoxide, cetylpyridinium hydroxide, n-butyltri-ethylphosphonium phenoxide, tetraethylphosphonium hydroxide and tetra-n-butlyammonium hydroxide.

29. The method of claim 1, where the diazomethane precursor comprises a N-methyl N nitroso compound or comprises a precursor of a N-methyl N nitroso compound.

30. The method of claim 1, where the diazomethane precursor comprises one or more than one substance selected from the group consisting of N-methyl-N-nitroso urea, N-[N'-methyl-N'-nitroso(aminomethyl)]benzamide, N-nitroso-β-methylaminoisobutyl methyl ketone, N,N'-dimethyl-N,N'-dinitrosoterephthalamide; and 1-methyl-3-nitro-1-nitrosoguanadine.

31. A method as claimed in claim 1, where the diazomethane precursor comprises N-methyl-N-nitroso-toluenesulphonamide.

32. The method of claim 5, where the second solvent comprises a polar solvent.

33. The method of claim 7, where the sparge diluent gas comprises one or more than one gas selected from the group consisting of an inert gas, carbon dioxide and air.

34. The method of claim 7, where the sparge diluent gas comprises one or more than one gas selected from the group consisting of argon, helium and nitrogen.

35. The method of claim 7, where the sparge diluent gas is nitrogen.

36. The method of claim 14, where the temperature is between about 25° C. and about 70° C.

37. The method of claim 14, where the temperature is about 40° C.

38. The method of claim 1, further comprising the step of feeding the waste stream into a quench tank containing an acid medium; and where the acid medium is selected to react with residual gaseous diazomethane in the waste stream, thereby producing reaction products that do not include diazomethane.

39. The method of claim 38, where the quenched tank is maintained at a pH between about 4 and about 6.

40. The method of claim 38, where the quenched tank is maintained at a pH of about 5.5.

41. The method of claim any of claim 38, where the acid medium comprises one or more than one acid selected from the group consisting of an inorganic acid and an aqueous solution of an organic acid.

42. The method of claim 38, where the acid medium comprises acetic acid.

43. The method of claim 1, where the reactor vessel in the feeding step comprises a stainless steel reactor vessel comprising:

a) a base having a full bore bursting disk connected to a quench tank;

b) a heat transfer surface connected to a heating means, a cooling means or both a heating means and a cooling means;

c) a thermoprobe inside the reactor vessel;

d) a waste outlet valve situated between the base of the reactor vessel and the quench tank;

e) addition ports in the reactor vessel configured to supply make-up materials to the head space of the reactor; and f) a top-surface diluent gas sparge port in the reactor vessel configured to supply diluent gas below to the head space of the reactor;

g) a bottom surface diluent gas sparge port in the reactor vessel configured to supply diluent gas below the liquid level of the reactor; and h) a gas outlet port in the reactor vessel configured to recover gas from the head space of the reactor.

44. The method of claim 1, further comprising the step of using the gaseous diazomethane gas in a downstream reaction.

45. The method of claim 1, further comprising the step of storing the gaseous diazomethane.

* * * * *

UNITED STATES PATENT AND TRADEMARK OFFICE
CERTIFICATE OF CORRECTION

PATENT NO. : 6,962,983 B2 Page 1 of 1
APPLICATION NO. : 10/129404
DATED : November 8, 2005
INVENTOR(S) : Antony John Warr et al.

It is certified that error appears in the above-identified patent and that said Letters Patent is hereby corrected as shown below:

Column 7:
line 58: replace "claim 1" with --claim 2--
line 67: replace "claim 1" with --claim 2--

Column 8:
line 8: replace "below" with --above--
line 34: replace "claim 1" with --claim 2--

Column 9:
line 42: replace "claim 1" with --claim 2--

Column 10:
After Claim 45, line 45: add

--46. The method of claim 2, where the feeding step comprises simultaneously feeding the diazomethane precursor and the base into the reactor vessel; and
where the removing step comprises removing the gaseous diazomethane gas and the waste stream from the reactor vessel in a continuous stream.--

--47. The method of claim 1, where the feeding step comprises feeding either the diazomethane precursor, or the base, or both the diazomethane precursor and the base into the reactor vessel in an intermittent or pulsed stream; and
where the removing step comprises removing the gasous diazomethane gas from the reactor vessel in an intermittent or pulsed stream.--

Signed and Sealed this

Twelfth Day of September, 2006

JON W. DUDAS
*Director of the United States Patent and Trademark Office*